United States Patent

Dheer et al.

[11] 4,148,785
[45] Apr. 10, 1979

[54] ANALGESIC POLYPEPTIDE

[75] Inventors: Surendra K. Dheer, King of Prussia; William H. McGregor, Malvern, both of Pa.

[73] Assignee: American Home Products Corporation, New York, N.Y.

[21] Appl. No.: 886,979

[22] Filed: Mar. 15, 1978

[51] Int. Cl.² .................... C07C 103/52; A61K 37/00
[52] U.S. Cl. .............................. 260/112.5 R; 424/177
[58] Field of Search ................ 260/112.5 R; 424/177

[56] References Cited

PUBLICATIONS

Baxter, et al., British J. of Pharmacology, Mar. 2, 1977, pp. 455P–456P and 523P.
Coy, et al, B.B.R.C., 73, 632 (1976).

Primary Examiner—Delbert R. Phillips
Attorney, Agent, or Firm—Richard K. Jackson

[57] ABSTRACT

The polypeptides of the formula:

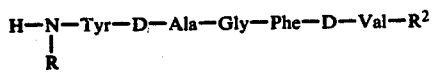

in which
R is hydrogen, methyl, allyl or cyclopropylmethyl; and
$R^2$ is —OH, —$NH_2$ or —$NHC_nH_{2n+1}$ where n is 1,2,3 or 4 or a pharmaceutically acceptable salt thereof, exert an analgesic effect in warm-blooded animals when peripherally administered.

5 Claims, No Drawings

ANALGESIC POLYPEPTIDE

BACKGROUND OF THE INVENTION

Enkephalin, a natural opiate receptor agonist in the brain, has been identified [see Hughes et al., *Nature*, 256, 577(1976)] as a mixture of two pentapeptides: H—Tyr—Gly—Gly—Phe—Met—OH (methionine-enkephalin) and H—Tyr—Gly—Gly—Phe—Leu—OH (leucine-enkephalin). Both peptides mimic the ability of morphine to block electrically evoked contractions of mouse vas deferens and guinea pig ileum, and both inhibit the sterospecific receptor binding of the opiate antagonist 3H-naloxone in brain homogenates.

It has been proposed that enkephalin receptors may be sites at which morphine-like drugs exert their analgesic activities, and that enkephalin may be the modulator or transmittor in brain systems for pain suppression or analgesia. It has been reported that methionine-enkephalin and leucine-enkephalin, when administered by injection in the brain ventricle in rats, induce a profound analgesia that is fully reversible by naloxone. [See Beluzzi et al., *Nature*, 260, 625(1976)]. The enkephalins are inactive when administered peripherally, however, and it is believed that the enkephalins are rapidly destroyed by blood enzymes and/or are poorly transported across the blood-brain barrier.

The amino acid sequence of methionine-enkephalin is identical to that of the N-terminal portion of the C-fragment ($\beta$-endorphin or $\alpha$-LPH[61–91]) of the peptide $\beta$-lipotropin, which is found in large concentrations in the pituitary and in much lower concentrations in th brain. Other naturally-occuring fragments of $\beta$-lipotropin are known, for example: $\alpha$-endorphin ($\beta$-LPH[61–76]) and $\gamma$-endorphin ($\beta$-LPH[61–77]). Both $\beta$-liptropin and the endorphins show morphine-like properties in various test systems, and it has been suggested that methionine-enkephalin is a breakdown product of the large opiate-like peptides. Enkephaline, its relationship to $\beta$-lipotropin and the endorphins, and the pharmacological properties thereof, are reviewed in an article by Iversen et al., *Nature*, 262, 738(1976). Recent developments are also described in detail in the "Proceedings of the International Narcotics Research Club Meeting, Abderdeen, U. K., July 19–22, 1976," published in *OPIATES AND ENDOGENOUS OPIOID PEPTIDES*, North Holland Publishing Company, Amsterdam, 1976.

Various structural variations of methionine-enkephalin and leucine-enkephalin are described in the literature. For example, the pentapeptide N—Tyr—Gly—Gly—Phe—Thr—OH, wherein the fifth amino acid residue (methionine or luecine) is replaced by threonine, is described by Chang et al., *Life Sciences*, 18, 1473(1976). Similarly, a long acting synthetic pentapeptide, Tyr—D—Ala—Gly—Phe—Met—amide is described in Pert et al., *Science*, 194, 330 (1976); which compound, like the natural enkephalins, is inactive when administered peripherally. Baxter et al., *British Journal of Pharmacology*, March 2, 1977, pages 455P–456P and 523P report activity in the compound Tyr—D—Ala—Gly—Phe—D—Leu when administered intracerebroventricularly. Coy et al. B.B.R.C. 73 632(1976) disclose that D-Met[5] enkephalin has one tenth the activity of Met enkephalin.

DESCRIPTION OF THE INVENTION

In accordance with this invention, there is provided a group of polypeptides of the formula:

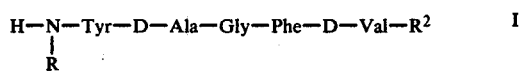

in which
R is hydrogen, methyl, allyl or cyclopropylmethyl; and
$R^2$ is —OH, —$NH_2$ or —$NHC_nH_{2n+1}$ where n is 1,2,3 or 4
or a pharmaceutically acceptable salt thereof.

All chiral amino acid residues in formula I and throughout this disclosure are in the natural or L-configuration unless otherwise indicated.

The preferred compounds are those of formula II:

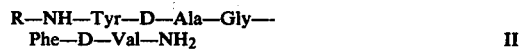

where R is hydrogen, methyl, allyl or cyclopropylmethyl, or a pharmaceutically acceptable acid addition salt thereof.

The pharmaceutically acceptable salts of the polypeptides of this invention are acid addition salts of the free base in which the acid may be either organic or inorganic, as for example, hydrochloric, phosphoric, maleic, acetic, citric, succinic, malic, and similar acids. Likewise, salts of the free peptidic acid are embraced by the expression "pharmaceutically acceptable salts", and include the sodium, potassium, ammonium, and lower alkylamine salts. The salts are prepared and isolated by conventional methods.

The analgesic polypeptides of this invention are prepared by classical and/or typical solid phase procedures employing either a benzhydrylamine polystyrene based resin for the production of the C-terminal amides or a chloromethylated or hydroxy methylated divinyl benzene crosslinked polystyrene resin for production of the C-terminal carboxylic acid or lower alkylamides. The polypeptide is removed from the resin support with HF and purified by gel filtration.

The N-substituted tyrosine reactants employed in the production of the compounds disclosed herein are readily prepared by reaction of methylchloride, allylchloride or cyclopropylmethyl chloride with a Boc-tyrosyl ester in the presence of silver oxide. The product is then saponified and hydrolyzed to obtain the desired reactant.

The analgesic activity of the polypeptides of this invention was demonstrated by the method of D-Amour and Smith, J. Pharmacol. Exp. Ther., 72, 74 (1941). The representative polypeptide of this invention Tyr—D—Ala—Gly—Phe—D—Val—$NH_2$, gave the following results in the reference standard rat tail flick test:

| Dose Intravenous milligram/kilogram | Response No. showing analgesia/No. tested minutes after administration | | |
|---|---|---|---|
| | 15 | 30 | 60 |
| 5.0 | 6/6 | 5/6 | 0/5 |
| 2.5 | 5/6 | 3/5 | 3/5 |
| 1.0 | 2/6 | 1/6 | 0/6 |
| .5 | 4/6 | 4/6 | 1/6 |
| .25 | 1/6 | 0/6 | 1/6 |

| Subcutaneous | minutes after administration | | | |
|---|---|---|---|---|
| milligram/kilogram | 30 | 60 | 90 | 120 |
| 5.0 | 2/6 | 1/6 | 0/6 | 0/6 |
| 20.0 | 6/6 | 3/6 | 3/6 | 2/6 |

The test results demonstrate that the compounds of this invention induce analgesia upon administration of a single intravenous injection of about 0.5 milligrams per kilogram or more. For practical purposes, it is contemplated, based upon the preceding test results, that an intravenous dose of from about 0.5 to about 20 milligrams per kilogram in single or plural doses is the appropriate dosage to achieve that degree of analgesia desired for various application. By oral adminstration, a dosage of about 400 milligram per kilogram or more, produce the desired effect. The exact dose to be employed will, of course, vary somewhat with the specific compound employed, the patient and the degree of analgesia desired. The determination of a precise dose for production of a desired effect is readily determined empirically by the physician.

The following examples illustrate the preparation of the polypeptides of the invention.

EXAMPLE I

Tert-butyloxycarbonyl-O-benzyl-L-tyrosyl-D-alanylglycyl-L-phenylalanyl-hydroxymethyl polystyrene Chloromethylated polystyrene resin (60 g.; 54 mM) was esterified with 2.5 equivalents of Cs-salt of t-Boc-L-phenylalanine according to Gisin [Helv. Chim. Acta., 56, 1476 (1973)]. The polystyrene ester (70.2 g.) was then coupled with t-Boc—Gly—OH, t-Boc—D—Ala—OH, and t-Boc—OBzl—Tyr—OH according to the following schedule.
1. Washed with $CH_2Cl_2 \times 3$.
2. Treated with 50% trifluoroacetic acid (TFA)/$CH_2Cl_2$ containing 0.5% dithioerythritol (DTE) for five minutes.
3. Treated with 50% trifluoroacetic acid (TFA)/$CH_2Cl_2$ containing 0.5% dithioerythritol (DTE) twice, fifteen minutes each.
4. Washed with $CH_2Cl_2 \times 3$ two minutes each.
5. Washed with dimethylformamide (DMF)$\times 2$ two minutes each.
6. Treated with 12% triethylamine (TEA) in dimethylformamide (DMF) for one minute.
7. Treated with 12% triethylamine (TEA) in dimethylformamide for 10 minutes.
8. Washed with dimethylformamide (DMF)$\times 3$ for two minutes each.
9. Washed with MeOH$\times 2$ two minutes each.
10. Washed with $CH_2Cl_2 \times 3$ for two minutes each.
11. Added Boc amino acid in $CH_2Cl_2$ and stirred for five minutes.
12. Added one-half equivalent of diisopropylcarbodiimide (DIC) and stirred for thirty minutes.
13. Added the other half equivalent of diisopropylcarbodiimide and stirred overnight.
14. Washed with $CH_2Cl_2 \times 3$ for two minutes each.
15. Checked for completeness of coupling with ninhydrin (Kaiser et al., Anal. Biochem., 34, 595, 1970).
16. Washed with MeOH$\times 3$ for two minutes each.
17. Washed with $CH_2Cl_2 \times 3$ for two minutes each.

EXAMPLE II

Tert-butyloxycarbonyl-O-benzyl-L-tyrosyl-D-alanylglycyl-L-phenylalanine hydrazide b The procedure used was adapted from Ohno et al. (J. Am. Chem. Soc, 89, 599, 4, 1967).

Tertiary butyloxycarbonyl-O-benzyl-L-tyrosyl-D-alanylglycyl-L-phenylalanyl hydroxymethyl polystyrene (50 g.) of example I was dried in vacuo, suspended in 250 ml. of dimethylformamide and stirred with 37 g. (30 mM) hydrazine hydrate (95%) for 2 days at room temperature. The resin was filtered and washed with dimethylformamide. The filtrate and washings were pooled and evaporated to dryness in vacuo. The residual gum was treated with water and the white solid collected by filtration. The solid was crystallized from methanol. After four such crystallizations, 14.4 g. of peptide hydrazide was obtained.

Elemental Analysis — Calc'd.: C, 58.95; H, 6.67; N, 14.74. Found: C, 62.31; H, 6.40; N, 12.62.

TLC: (silica gel F, 250 $\mu$ plates)
$CHCl_3$:MeOH (9:1), $R_f=0.10$
n-BOOH:AcOH:$H_2O$ (4:1:5), $R_f=0.34$
EtOH:$H_2O$ (7:3), $R_f=0.06$ TLC plates were developed by spraying first with HCl followed by the Tollen's and peptide reagent.

EXAMPLE III

L-tyrosyl-D-alanylglycyl-L-phenylalanyl-D-valine amide

T-Boc-L-O-Bzl-Tyrosyl-D-alanylglycyl-L-phenylalanyl hydrazide (1.0 g; 1.51 mM) of example II was dissolved in 5 ml. of DMF, cooled to −20° C. and 1 ml. of 4N hydrochloric acid (4mM) in dioxane was added (Sieber et al., Helv. Chim. Acta, 53, 2135 (1970).) The temperature was raised to −15° C. and 5-butylnitrite (223 $\mu$l) was added. After stirring the mixture for 10 min. at −10° C., the formation of azide was checked with Tollen's reagent. A solution of 175 mg. of D-Val—$NH_2$ (1.51 mM) in 6 ml. of DMF was added at −15° C. followed by 1.3 ml. of ethyldiisopropylamine (in 6 portions). The basic reaction mixture was left for 3 days at 4° C. and then added to ice-cold 1% acetic acid. The solid was collected by filtration, dissolved in 5% AcOH and chromatographed on a 2.5×150 cm G-10 Sephadex column preequilibrated in 5% AcOH. Fractions 109–128 were pooled and freeze-dried to obtain 281 mg. of L-Tyr—D-Ala-Gly—Phe—D-Val—$NH_2$.

Amino Acid Analysis—Tyr (1.02), D-Ala (1.04), Gly (1.00), Phe (0.90), D-Val (0.80).

TLC (silica gel F, 250 $\mu$)
n-BuOH:AcOH:$H_2O$ (4:1:5) $R_f=0.46$
EtOH:$H_2O$ (7:3) $R_f=0.75$
$CHCl_3$:MeOH:$NH_3$ (60:30:5) $R_f=0.50$

EXAMPLE IV

D-Val-$NH_2$

D-Val—$NH_2$ was prepared by dissolving tert-butyloxycarbonyl-D-valine (10.0 g.; 46.1 mM) in 100 ml. of THF and treating the solution with 1,1'-carbonyl-diimidazole (8.2 g.; 50.7 mM) for four hours. Tetrahydrofuran (150 ml.) saturated with ammonia was added and the reaction mixture was left at 4° C. overnight. The THF was removed in vacuo and the residue was crystallized twice from ethylacetate-hexane mixture at 0° C. The crystals obtained were collected by filtration (3.5 g.).

Elemental Analysis Calc'd.: C, 55.56; H, 9.25; N, 13.0. Found: C, 55.61; H, 9.26; N, 13.05.

TLC: (silica gel F; 250 μ)
n-BuOH:NH$_3$:H$_2$O (4:1:5), R$_f$=0.64
CHCl$_3$:MeOH (9:1), R$_f$=0.47
CHCl$_3$:MeOH:NH$_3$ (60:30:5), R$_f$=0.91
EtOH:H$_2$O (7:3) R$_f$=0.84

The tertiary butyloxycarbonyl-D-Val—NH$_2$ was treated with 50% trifluoroacetic acid (TFA) in methylene dichloride for one hour at room temperature. Excess TFA and methylene dichloride were removed in vacuo. The residual semi-solid was dissolved in anhydrous DMF and used as such for the coupling reaction of Example III.

EXAMPLE V

L-Tyrosyl-D-alanyl-glycyl-L-phenylalanyl-D-valine—OH

Chloromethylated polystyrene resin is esterified with Boc—D-Val—OH according to the procedure of *Gisin, Helv. Chim. Acta.*, 56, 1976 (1973) and the polymeric ester is treated according to the procedure of example 1 for incorporation of Boc—Phe—OH, Boc—Gly—OH, Boc—D—Ala—OH and Boc—Tyr(Bzl)—OH. The resulting peptido resin is treated according to the procedure of example III to yield the title pentapeptide acid.

EXAMPLE VI

L-Tyrosyl-D-alanyl-glycyl-L-phenylalanyl-D-valine ethylamide

Treatment of the peptido resin of example V with ethylamine in a sealed flask for 10 hours followed by removal of excess ethylamine, extraction with DMF filtration and evaporation of the filtrate yields the title ethylamide.

EXAMPLE VII

N-methyl-L-tyrosyl-D-alanyl-glycyl-L-phenylalanyl-D-valine amide

The procedure of example V is repeated, with the exception that the last amino acid introduced into the solid phase reactor is Boc—N-methyl—L-tyrosyl(Bzl)—OH. The peptido resin is cleaved and worked up in accordance with the procedure of example III to yield the title compound.

What is claimed is:

1. A polypeptide of the formula:

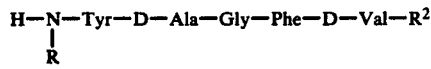

in which

R is hydrogen, methyl, allyl or cyclopropylmethyl; and

R$^2$ is —NH$_2$ or —NHC$_n$H$_{2n+1}$ where n is 1,2,3, or 4 or a pharmaceutically acceptable salt thereof.

2. A compound of claim 1 of the formula:

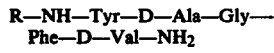

where R is hydrogen, methyl, allyl or cyclopropylmethyl, or a pharmaceutically acceptable acid addition salt thereof.

3. The compound of claim 1 which is Tyr—D-Ala—Gly—Phe—D-Val—NH$_2$ or a pharmaceutically acceptable salt thereof.

4. The compound of claim 1 which is Tyr—D-Ala—Gly—Phe—D-Val—NHC$_2$H$_5$ or a pharmaceutically acceptable salt thereof.

5. The compound of claim 1 which is N-methyl—Tyr—D-Ala—Gly—Phe—D-Val—NH$_2$ or a pharmaceutically acceptable salt thereof.

* * * * *